US006242214B1

(12) United States Patent
Bandman et al.

(10) Patent No.: US 6,242,214 B1
(45) Date of Patent: Jun. 5, 2001

(54) HUMAN GTPASE-ASSOCIATED PROTEINS

(75) Inventors: Olga Bandman, Mountain View; Preeti Lal, Santa Clara; Karl J. Guegler, Menlo Park; Neil C. Corley; Chandra Patterson, both of Mountain View, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/063,743

(22) Filed: Apr. 21, 1998

(51) Int. Cl.[7] .............................. C12P 21/06; C12Q 1/68; C12N 15/00; C12N 1/20; C07H 21/02

(52) U.S. Cl. ........................ 435/69.1; 435/6; 435/91.2; 435/252.3; 435/320.1; 536/23.1

(58) Field of Search ..................... 536/23.1; 435/320.1, 435/252.3, 69.1, 6, 91.2

(56) References Cited

U.S. PATENT DOCUMENTS 5,366,889 * 11/1994 MacDonald et al. .............. 435/252.3

OTHER PUBLICATIONS

Accessions No. AA881621, Mar. 26, 1998.*
Lodish, H. et al., *Molecular Cell Biology*, Scientific American Books, Inc., New York, NY, pp. 876–877 (1995).
Neer, E.J. et al., "The ancient regulatory–protein family of WD–repeat proteins", *Nature*, 371: 297–300 (1994).
Spiegel, A.M., "Inborn errors of signal transduction: Mutations in G proteins and G protein–coupled receptors as a cause of disease", *J. Inher. Metab. Dis.*, 20: 113–121 (1997).
Müller, S. et al., "Interactions of Phosducin with Defined G Protein βγ–Subunits", *J. Biol. Chem.*, 271: 11781–11786 (1996).

Meij, J.T.A., "Regulation of G protein function: Implications for heart disease", *Mol. Cell. Biochem.*, 157: 31–38 (1996).
Watson, A.J. et al., "A Fifth Member of the Mammalian G–Protein β–Subunit Family", *J. Biol. Chem.*, 269: 22150–22156 (1994).
Garcia–Higuera, I. et al., "Folding of Proteins with WD–Repeats: Comparison of Six Members of the WD–Repeat Superfamily to the G Protein βSubunit", *Biochemistry*, 35: 13985–13994 (1996).
Aussel, C. et al., "Inhibition and Activation of Interleukin 2 Synthesis by Direct Modification of Guanosine Triphosphate–Binding Proteins", *J. Immunol.*, 140: 215–220 (1988).
Vitale, G. et al., "The GDP/GTP Cycle of Rab5 in the Regulation of Endocytotic Membrane Traffic", *Cold Spring Harbor Symp. Quant. Biol.*, 60: 211–220 (1995).
Vitale, G. et al., "Distinct Rab–binding domains mediate the interaction of Rabaptin–5 with GTP–bound rab4 and rab5", *EMBO J.*, 17: 1941–1951 (1998).
Rounsley, S.D. et al., (Direct Submission), GenBank Sequence Database (Accession AC002333), National Center for Biotechnology Information, National Library of Medicine, Bethesda, Maryland, 20894, (GI 2281081; GI 2281093).
Katz, A. et al., "Subunits βγ of heterotrimeric G protein activate β2 isoform of phospholipase C", *Nature*, 360: 686–689 (1992).

(List continued on next page.)

*Primary Examiner*—Karen Cochrane Carlson
*Assistant Examiner*—Devesh Srivastava
(74) *Attorney, Agent, or Firm*—Incyte Pharmaceuticals, Inc.

(57) ABSTRACT

The invention provides human GTPase-associated proteins (GPAP) and polynucleotides which identify and encode GPAP. The invention also provides expression vectors, host cells, antibodies, agonists, and antagonists. The invention also provides methods for diagnosing, treating or preventing disorders associated with expression of GPAP.

10 Claims, 10 Drawing Sheets

```
1   M I E Q Q K R K G P E L P L V P V K R Q R H S L L L G A Q S¹    059953
1   M E I N S R E N E T A L S - C P R P M E W S T V P H S A S Q   GI 2281093

31  G P G A G Q Q Q A T P G A L L Q A G P P R C S S L Q A P I M    059953
30  G P G P - - - - - - - - - - - N C K N R T S S L E A P I M     GI 2281093

61  L L S G H E G E V V C C K F H P N G S T L A S A G F D R L I¹   059953
48  L L S G H P S A V Y T M K F N P A G T L I A S G S H D R E I   GI 2281093

91  L L W N V Y G D C D N Y A T L K C H S G A V M E L H Y N T D    059953
78  F L W R V E G D C K N F M V L K G H K N A I L D L H W T S D   GI 2281093

121 G S M L F S A S T D K T V A V W D S E T G E R V K R L K G H    059953
108 G S Q I V S A S P D K T V R A W D V E T G K Q I K K M A E H   GI 2281093

151 T S F V N S C Y P A R R G P Q L V C T G S D D G T G K L W D    059953
138 S S F V N S C C P T R R G P P L I I S C S D D G T A K L W D   GI 2281093

181 I R K K A A I Q T F Q N T Y Q V L A V T P N D T S D Q I I S    059953
168 M R Q R G A I Q T F P D K Y Q I T A V S F S D A A D K I F T   GI 2281093

211 G G I D N D I K V W D L R Q N K L T Y T M R G E A D S V T G¹   059953
198 G G V D N D V K V W D L R K G E A T M T L E G H Q D T I C G   GI 2281093

241 L S L S S E G S Y L L S N A M D N T V R V W D V R P F A P K    059953
228 M S L S P D G S Y L L T N G M D N X L C V W D M R P Y A P Q   GI 2281093

271 E R C V K I F Q G N V H N F E K N L L R C S W S P D G S K -    059953
258 N R C V K I P E G H Q H N F E K N L L R C S W S P D G T K V   GI 2281093

301 A A G S A D R F V Y V W D T T S R R I L Y K L P G H A G S I    059953
288 T A G S D R M V H I W D T T S R R T I Y K L P G H T G S V   GI 2281093

331 N E V A P H P D E P I I I S A S S D K R L Y M G E F S E D M    059953
318 N E C V P H P T E P I I G S C S S D K N I Y L G E I          GI 2281093

361 D W K T P R L L V F E P Q T A                                  059953
343                                                              GI 2281093
```

OTHER PUBLICATIONS

Berridge, M.J. et al., "Changes in the levels of inositol phosphates after agonist–dependent hydrolysis of membrane phosphoinositides", *Biochem. J.*, 212: 473–482 (1983).

Vitale, G. et al., (Direct Submission), GenBank Sequence Database (Accession S83364), National Center for Biotechnology Information, National Library of Medicine, Bethesda, Maryland, 20894, (GI 1911773; GI 1911774).

* cited by examiner

FIGURE 1A

```
                  9          18         27         36         45         54
5'  CCC ACG CGT  CCG CCC ACG  CGT CCG GCG  CTG AAG AGA  CCG GTT GCC  GCC ATG
                                                                              M 63         72         81         90         99         108
    ATA GAA CAG  CAG AAG CGT  AAG GGC CCA  GAG TTG CCG  CTG GTT CCA  GTC AAG CGG
    I   E   Q    Q   K   R    K   G   P    E   L   P    L   V   P    V   K   R 117        126        135        144        153        162
    CAG CGG CAT  GAG TTG CTG  TTG GGA GCG  CCA GGG TCT  GCC CCA GGA  GCC GGG CAG CAG
    Q   R   H    E   L   L    L   G   A    P   G   S    A   P   G    A   G   Q   Q 171        180        189        198        207        216
    CAG GCG ACG  CCG GGA GCC  TTG CTG CTG  CAA GCG CCT  CCA AGA TGT  TCC TCC CTT
    Q   A   T    P   G   A    L   L   L    Q   A   P    P   R   C    S   S   L 225        234        243        252        261        270
    CAA GCC CCA  ATC ATG CTG  CTC TCT GGA  CAT GAA GGG  GAA GTC TAC  TGC TGC AAG
    Q   A   P    I   M   L    L   S   G    H   E   G    E   V   Y    C   C   K 279        288        297        306        315        324
    TTC CAC CCC  AAC GGA TCC  ACC TTA GCA  TCT GCA GGA  TTT GAC CGA  CTG ATA TTA
    F   H   P    N   G   S    T   L   A    S   A   G    F   D   R    L   I   L 333        342        351        360        369        378
    CTG TGG AAT  GTC TAT GGT  GAC TGT GAT  AAC TAT GCC  ACA CTG AAG  GGA CAC AGT
    L   W   N    V   Y   G    D   C   D    N   Y   A    T   L   K    G   H   S
```

```
         387            396        405        414        423        432
GGA GCA GTG ATG GAA TTG CAT TAC AAC ACA GAT GGC AGT ATG CTT TTC TCA GCA
 G   A   V   M   E   L   H   Y   N   T   D   G   S   M   L   F   S   A 441            450        459        468        477        486
TCC ACA GAT AAA ACC GTG GCT GTG TGG GAT AGT GAA ACA GGT GAG AGG GTT AAA
 S   T   D   K   T   V   A   V   W   D   S   E   T   G   E   R   V   K 495            504        513        522        531        540
AGG CTA AAG GGA CAT ACT TCC TTT GTG AAT TCC TGT TAT CCA GCC AGG AGA GGC
 R   L   K   G   H   T   S   F   V   N   S   C   Y   P   A   R   R   G 549            558        567        576        585        594
CCT CAG CTT GTC TGC ACT GGC AGT GAT GGC GAT ACA GGT AAG CTT TGG GAC ATC
 P   Q   L   V   C   T   G   S   D   G   D   T   G   K   L   W   D   I 603            612        621        630        639        648
CGG AAG AAA GCA GCC ATC CAG ACA TTT CAG AAC ACG TAC CAG GTG TTA GCT GTG
 R   K   K   A   A   I   Q   T   F   Q   N   T   Y   Q   V   L   A   V 657            666        675        684        693        702
ACC TTC AAT GAC ACA AGT GAT CAG ATT ATT TCT GGT GGA ATA GAC AAT GAT ATC
 T   F   N   D   T   S   D   Q   I   I   S   G   I   D   N   D   I 711            720        729        738        747        756
AAG GTC TGG GAC CTG CGC CAG AAC AAG CTA ACC TAC ACC ATG AGA GGC CAT GCA
 K   V   W   D   L   R   Q   N   K   L   T   Y   T   M   R   G   H   A
```

FIGURE 1B

```
     765            774         783         792         801         810
GAT TCA GTG ACT GGC CTG AGT TTA AGT TCT GAA GGC TCT TAT CTT TTG TCC AAT
 D   S   V   T   G   L   S   L   S   S   E   G   S   Y   L   L   S   N 819            828         837         846         855         864
GCA ATG GAC AAT ACA GTT CGT GTC TGG GAT GTC CGG CCA TTT GCC CCC AAA GAG
 A   M   D   N   T   V   R   V   W   D   V   R   P   F   A   P   K   E 873            882         891         900         909         918
AGA TGT GTA AAG ATA TTT CAA GGA AAT GTG CAC AAC TTT GAA AAG AAC CTT CTG
 R   C   V   K   I   F   Q   G   N   V   H   N   F   E   K   N   L   L 927            936         945         954         963         972
AGA TGT TCT TGG TCA CCT GAT GGA AGC AAA ATA GCA GCT GGC TCA GCC GAC AGG
 R   C   S   W   S   P   D   G   S   K   I   A   A   G   S   A   D   R 981            990         999         1008        1017        1026
TTT GTT TAT GTG TGG GAT ACC ACA AGC AGG AGA ATA TTG TAT AAG CTG CCC GGC
 F   V   Y   V   W   D   T   T   S   R   R   I   L   Y   K   L   P   G 1035           1044        1053        1062        1071        1080
CAT GCT GGC TCC ATC AAT GAA GTG GCT TTC CAC CCT GAT GAG CCC ATC ATT ATC
 H   A   G   S   I   N   E   V   A   F   H   P   D   E   P   I   I   I 1089           1098        1107        1116        1125        1134
TCA GCA TCG AGT GAC AAG AGA CTG TAT ATG GGA GAG TTC AGT GAA GAT ATG GAC
 S   A   S   S   D   K   R   L   Y   M   G   E   F   S   E   D   M   D
```

FIGURE 1C

```
                        1143        1152            1161            1170            1179        1188
                    TGG AAG ACT CCA AGG CTG CTT GTC TTT GAG CCT CAG ACT GCA TAA GTG ATG CCA
                     W   K   T   P   R   L   L   V   F   E   P   Q   T   A 1197        1206
                    ATG TTG GAT GTC AGG CTA GCA CC 3'
```

FIGURE 1D

```
                                                  9                18                27                36                45                54
5' GGC CAG GTT GTG AGG AAC CGC AGC GCG CCG CAG GAC CGG GCC GCT GAG CCT GCA 63                72                81                90                99               108
   GCC GCC CCG CGC CGT GAC CTG CGA CCC TAG ACC CCG ACT CCC TTT GGC TCA GCC 117               126               135               144               153               162
   CGC GCG CCC CAG GCC CGG CCC GGG CGG CGC GAC GGG AGG ATG AGC GGC GGG CGG
                                                                      M   S   G   G   R 171               180               189               198               207               216
   CGG AAG GAG GAG CCG CCT CAG CCG CTG GCC AAC GGG GCC CTC AAA GTC TCC
       R   K   E   E   P   P   Q   P   L   A   N   G   A   L   K   V   S 225               234               243               252               261               270
   GTC TGG AGT AAG GTG CTG CGG AGC GAC GCG GCC TGG GAG GAT AAG GAT GAA TTT
       V   W   S   K   V   L   R   S   D   A   A   W   E   D   K   D   E   F 279               288               297               306               315               324
   TTA GAT GTG ATC TAC TGG TTC CGA CAG ATC ATT GCT GTG GTC CTG GGT GTC ATT
       L   D   V   I   Y   W   F   R   Q   I   I   A   V   V   L   G   V   I 333               342               351               360               369               378
   TGG GGA GTT TTG CCA TTA CGA GGG TTC TTG GGA ATA GCA GGA TTC TGC CTG ATC
       W   G   V   L   P   L   R   G   F   L   G   I   A   G   F   C   L   I
```

FIGURE 2A

```
            387       396       405       414       423       432
AAT GCA GGA GTC CTG TAC CTC TAC TTC AGC AAT TAC CTA CAG ATT GAT GAG GAA
 N   A   G   V   L   Y   L   Y   F   S   N   Y   L   Q   I   D   E   E 441       450       459       468       477       486
GAA TAT GGT GGC ACG TGG GAG CTC ACG AAG GAA GGG TTT ATG ACC TCT TTT GCC
 E   Y   G   G   T   W   E   L   T   K   E   G   F   M   T   S   F   A 495       504       513       522       531       540
TTG TTC ATG GTC ATT TGG ATC ATC TTT TAC ACT GCC ATC CAT TAT GAC TGA TGG
 L   F   M   V   I   W   I   I   F   Y   T   A   I   H   Y   D 549       558       567       576       585       594
TGT ACA GCT CCC AAG TGC TCC CTA TCC AGT CCA AAG GAC CCT CTT GAT TAC AGC 603       612       621       630       639       648
ACA GGA ACT TGA TCG TTG GGG AAC CCC AGC CCC TTG GAA CTT GGA AGA CCC GTG 657       666       675       684       693       702
TTT CCT GGA CCG CGA ATC AGT GTG TTG GGC ATC AGT GTT TTC TGC AAG GGT TGT 711       720       729       738       747       756
GAC CTG AAA CTT TTT AAA AAC CAC CCA CCT TTG GGG AAG CAT TTC TGA ATT TAT
```

FIGURE 2B

```
         765            774            783            792            801            810
CCA TCA CCA ACC ATT TCT TCT TGG ATA CCA TCA AGT AAC AGC TAT TAT TTG CCA 819            828            837            846            855            864
AGT GGA GCT GTC ATT TAA TTT GAT GCA CCT CTG GAT TCA GAT GAA ACA TTA AAT 873            882            891            900            909            918
TGT CTT CCT CGA TTC TCC ATC GGG TGT AGA GTT TTT AAA CTA TCA ATG GCA TTT 927            936            945            954            963            972
CAA GTC TTC TGA AAC AGC ATG GCT GTA TGT GCG TGG TCC ATA GCA CAG TAC ATG 981            990            999           1008           1017           1026
CAG CAT CTA ATA AGA GTT TCC ATT GTA GAA TGT TTT CAC ATA CTT GAA TAA ATC 1035           1044
AAA TCT TTA ATT GAG AAA AAA AAA AAA A 3'
```

FIGURE 2C

```
  1  MIEQQKRKGPELPLPLVPVKRQRHELLLGAGS            059953
  1  MEIMSRENETALS-GRPMEWSTVPHSASQ              GI 2281093

31  GPGAGQQQATPGALLQAGPPRCSSLQAPIM              059953
 30  GPGP---------NGKNRTSSLEAPIM                GI 2281093

61  LLSGHEGEVYCCKFHPNGSTLASAGFDRLI              059953
 48  LLSGHPSAVYTMKFNPAGTLIASGHDREI              GI 2281093

91  LLWNVYGDCDNYATLKGHSGAVMELHYNTD              059953
 78  FLWRVHGDCKNFMVLKGHKNAILDLHWTSD              GI 2281093

121  GSMLFSASTDKTVAVWDSETGERVKRLKGH              059953
108  GSQIVSASPDKTVRAWDVETGKQIKKMAEH              GI 2281093

151  TSFVNSCYPARRGPQLVCTGSDDGTGKLWD              059953
138  SSFVNSCCPTRRGPPLIISGSDDGTAKLWD              GI 2281093

181  IRKKAAIQTFQNTYQVLAVTFNDTSDQIIS              059953
168  MRQRGAIQTFPDKYQITAVSFSDAADKIFT              GI 2281093

211  GGIDNDIKVWDLRQNKLTYTMRGHADSVTG              059953
198  GGVDNDVKVWDLRKGEATMLEGHQDTITG              GI 2281093
```

HUMAN GTPASE-ASSOCIATED PROTEINS

FIELD OF THE INVENTION

This invention relates to nucleic acid and amino acid sequences of human GTPase-associated proteins and to the use of these sequences in the diagnosis, treatment, and prevention of cell proliferation disorders, autoimmune/inflammatory disorders, and vesicle trafficking disorders.

BACKGROUND OF THE INVENTION

The GTPase superfamily includes many proteins which act as intracellular switches in signal transduction and vesicle trafficking. (Lodish, H. et al. (1995) *Molecular Cell Biology*, Scientific American Books, Inc., New York, N.Y., pp. 876–877.) The family includes both heterotrimeric GTPases (G proteins) and low molecular weight GTPases related to Ras. In both cases the GTPase activity is regulated through interactions with other proteins.

The heterotrimeric G proteins, a family of peripheral membrane GTPases, are present in all cells. They control metabolic, humoral, neural, and developmental functions by transducing hormonal, neurotransmitter, and sensory signals into an array of cellular responses. Each G protein is composed of an alpha ($\alpha$), a beta ($\beta$), and a gamma ($\gamma$) subunit, associated as a complex in an inactive GDP-bound form. $G_\alpha$ binds GDP or GTP and contains the GTPase activity. The $\beta\gamma$ complex enhances binding of $G_\alpha$ to a receptor. $G_\gamma$ is necessary for the folding and activity of $G_\beta$. (Neer, E. J. et al. (1994) Nature 371:297–300.) Multiple homologs of each subunit have been identified in mammalian tissues, and different combinations of subunits have specific functions and tissue specificities. (Spiegel, A. M. (1997) J. Inher. Metab. Dis. 20:113–121.)

G protein activity is triggered by seven-transmembrane cell surface receptors (G protein coupled receptors; GPCRs) which respond to lipid analogs, amino acids and their derivatives, peptides, cytokines, and specialized stimuli such as light, taste, and odor. Activation of the receptor by its stimulus causes the replacement of the G protein-bound GDP with GTP. $G_\alpha$-GTP dissociates from the receptor and the $\beta\gamma$ complex. Both $G_\alpha$-GTP and the $\beta\gamma$ complex stimulate or inhibit effector molecules to transmit the signal delivered to the GPCR. The signaling is stopped when $G_\alpha$ hydrolyzes its bound GTP to GDP and reassociates with the $\beta\gamma$ complex. $G_\alpha$ interacts with the effectors adenylate cyclase, ion channels, and phospholipase C-$\beta$, and the $\beta\gamma$ complex interacts with adenylate cyclase, phospholipase C-$\beta$, $\beta$-adrenergic receptor kinase, phosducin, phosphoinositide 3-kinase, and potassium channels. In yeast, the $\beta\gamma$ complex mediates a G protein dependent mating response. (Müller, S. et al. (1996) J. Biol. Chem. 271:11781–11786; Meij, J. T. A. (1996) Mol. Cell. Biochem. 157:31–38; and Watson, A. J. et al. (1994) J. Biol. Chem. 269:22150–22156.)

$G_\beta$ proteins, also known as $\beta$ transducins, are all about 340 amino acids in length and contain seven tandem repeats of the WD-repeat sequence motif, a motif found in many proteins with regulatory functions. WD-repeat proteins contain from four to eight copies of a loosely conserved repeat of approximately 40 amino acids. Each repeat contains a central conserved region bracketed by Gly-His and Trp-Asp (WD) residues. The three-dimensional structure of the $\beta\gamma$ complex has been solved, and $G_\beta$ was shown to fold into a circular seven-bladed $\beta$ propeller. Other WD-repeat proteins are likely to form similar $\beta$ propeller structures. (Neer, supra; and Garcia-Higuera, I. et al. (1996) Biochemistry 35:13985–13994.)

Other proteins with seven WD repeats have been found, some of which have roles in signal transduction. Mutations in LIS1, a subunit of the human platelet activating factor acetylhydrolase, cause Miller-Dieker lissencephaly, a severe brain malformation. MSI1 is a negative regulator of Ras-mediated cAMP increase in yeast. RACK1 binds activated protein kinase C, and RbAp48 binds retinoblastoma protein. CstF is required for polyadenylation of mammalian pre-mRNA in vitro and associates with subunits of cleavage-stimulating factor. $\beta$Trcp is a yeast protein whose expression suppresses mutations in CDC15, a gene needed for normal anaphase in yeast. Uncharacterized 7 WD-repeat proteins exist as well. (Neer, supra.)

Research indicates that an irregularity in any GPCR pathway component can cause a physiological defect. (Meij, supra.) For example, mutations in the components of the cell signaling cascade as well as alterations in the expression pattern of these components may result in abnormal activation of leukocytes and lymphocytes, leading to the tissue damage and destruction seen in autoimmune diseases such as rheumatoid arthritis, biliary cirrhosis, hemolytic anemia, lupus erythematosus, and thyroiditis. T cell activation is a G protein regulated process. (Aussel, C. et al. (1988) J. Immunol. 140:215–220.)

Irregularities in G protein signaling also have a role in abnormal cell proliferation. Cyclic AMP stimulation of brain, thyroid, adrenal, and gonadal tissue proliferation is regulated by G proteins. Mutations in $G\beta$ subunits have been found in growth-hormone-secreting pituitary somatotroph tumors, hyperfunctioning thyroid adenomas, and ovarian and adrenal neoplasms. (Spiegel, supra.)

Other genetic disorders caused by loss or gain of function mutations in $G_\alpha$ subunits include Albright hereditary osteodystrophy, pseudohypoparathyroidism type Ia with precocious puberty, McCune-Albright syndrome, and congenital night blindness. (Spiegel, supra.) GPCR mutations are responsible for many diseases including color blindness, retinitis pigmentosa, congenital night blindness, nephrogenic diabetes insipidus, familial adrenocorticotropic hormone (ACTH) resistance, hypergonadotropic ovarian dysgenesis, familial male precocious puberty, male pseudohermaphroditism, sporadic hyperfunctional thyroid nodules, familial nonautoimmune hyperthyroidism, familial hypothyroidism, familial hypocalciuric hypercalcemia/neonatal severe primary hyperparathyroidism, familial hypoparathyroidism, congenital bleeding, Hirschsprung disease, Jansen metaphyseal chondrodysplasia, and familial growth hormone deficiency. (Spiegel, supra.) A G-protein controlled pathway, the $\beta$-adrenoreceptor/adenylate cyclase pathway, appears to be desensitized in heart failure. (Meij, supra.)

Rab proteins, which are Ras-related low molecular weight GTPases, regulate vesicular transport between subcellular compartments of eukaryotic cells. During this process, vesicles bud from a donor membrane and fuse with a recipient to deliver internalized materials. Rab proteins assist the binding of transport vesicles to their accepter organelles and initiate the vesicle fusion process using the energy from GTP hydrolysis. More than 30 Rab proteins have been identified in a variety of species, and each has a characteristic intracellular location and distinct transport function. Rab5 is localized to endosomes and regulates the fusion of early endosomes into late endosomes. Rab5 function in vesicular transport requires the cooperation of other proteins, including Rab-escort proteins, Rab-specific guanine nucleotide dissociation inhibitor, and rabaptins. (Vitale, G. et al. (1995) Cold Spring Harbor Symp. Quant. Biol.

60:211–220; and Vitale, G. et al. (1998) EMBO J. 17:1941–1951.) Several putative Rab5-interacting proteins expressed in human HeLa cells have been identified using a yeast two-hybrid screen, and their partial nucleotide and amino acids sequences determined. (Vitale (1995) supra.)

Defects in protein trafficking to organelles or the cell surface are involved in numerous human diseases and disorders. Defects in the trafficking of membrane-bound receptors and ion channels are associated with cystic fibrosis (cystic fibrosis transmembrane conductance regulator), glucose-galactose malabsorption syndrome ($Na^+$/glucose cotransporter), hypercholesterolemia (low-density lipoprotein receptor), and forms of diabetes mellitus (insulin receptor). Abnormal hormonal secretion is linked to disorders including diabetes insipidus (vasopressin), hyper- and hypoglycemia (insulin, glucagon), Grave's disease and goiter (thyroid hormone), and Cushing's and Addison's diseases (ACTH).

Cancer cells secrete excessive amounts of hormones or other biologically active peptides. Disorders related to this excessive secretion include: fasting hypoglycemia due to increased insulin secretion from insulinoma-islet cell tumors; hypertension due to increased epinephrine and norepinephrine secreted from pheochromocytomas of the adrenal medulla and sympathetic paraganglia; and carcinoid syndrome, which includes abdominal cramps, diarrhea, and valvular heart disease, caused by excessive amounts of vasoactive substances (serotonin, bradykinin, histamine, prostaglandins, and polypeptide hormones) secreted from intestinal tumors. Ectopic synthesis and secretion of biologically active peptides includes ACTH and vasopressin in lung and pancreatic cancers, parathyroid hormone in lung and bladder cancers, calcitonin in lung and breast cancers, and thyroid-stimulating hormone in medullary thyroid carcinoma.

The discovery of new human GTPase-associated proteins and the polynucleotides encoding them satisfies a need in the art by providing new compositions which are useful in the diagnosis, treatment, and prevention of cell proliferation disorders, autoimmune/inflammatory disorders, and vesicle trafficking disorders.

SUMMARY OF THE INVENTION

The invention features substantially purified polypeptides, human GTPase- associated proteins, referred to collectively as "GPAP-1" and individually as "GPAP-1" and "GPAP-2." In one aspect, the invention provides a substantially purified polypeptide comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant having at least 90% amino acid identity to the amino acid sequences of SEQ ID NO: 1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO: 1, and a fragment of SEQ ID NO:3. The invention also includes an isolated and purified polynucleotide variant having at least 90% polynucleotide sequence identity to the polynucleotide encoding the polypeptide comprising an amino acid sequence selected from the group consisting of SEQ ID NO: 1, SEQ ID NO:3, a fragment of SEQ ID NO: 1, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO: 1, SEQ ID NO:3, a fragment of SEQ ID NO:1, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide having a sequence which is complementary to the polynucleotide comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:3, a fragment of SEQ ID NO:1, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:3, a fragment of SEQ ID NO:1, and a fragment of SEQ ID NO:3, as well as a purified agonist and a purified antagonist to the polypeptide. The invention also provides a method for treating or preventing a cell proliferation disorder associated with the decreased expression or activity of GPAP, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a cell proliferation disorder associated with the increased expression or activity of a GPAP, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an autoimmune/inflammatory disorder associated with the decreased expression of activity of a GPAP, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an autoimmune/inflammatory disorder associated with the increased expression or activity of a GPAP, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a vesicle trafficking disorder, the method comprising administering to a subject in need of such treatment an effective amount of a pharmaceutical composition comprising a substantially purified polypeptide having an amino acid sequence of SEQ ID NO:3 or a fragment of SEQ ID NO:3.

The invention also provides a method for detecting a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of GPAP-1. The alignments were produced using MacDNASIS PROTM software (Hitachi Software Engineering Co. Ltd., San Bruno, Calif.).

FIGS. 2A, 2B, and 2C show the amino acid sequence (SEQ ID NO:3) and nucleic acid sequence (SEQ ID NO:4) of GPAP-2.

FIGS. 3A and 3B show the amino acid sequence alignment between GPAP-1 (Incyte Clone number 059953; SEQ ID NO:1) and Arabidopsis thaliana beta transducin isolog (GI 2281093; SEQ ID NO:5). The alignments were produced using the multisequence alignment program of LASERGENE™ software (DNASTAR Inc, Madison Wis.).

FIG. 4 shows the amino acid sequence alignment between GPAP-2 (Incyte Clone number 2908824; SEQ ID NO:3) and human putative Rab5-interacting protein {clone L1-57} (GI 1911774; SEQ ID NO:6).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"GPAP," as used herein, refers to the amino acid sequences of substantially purified GPAP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to GPAP, increases or prolongs the duration of the effect of GPAP. Agonists may include proteins, nucleic acids, carbohydrates, or any other molecules which bind to and modulate the effect of GPAP.

An "allelic variant," as this term is used herein, is an alternative form of the gene encoding GPAP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding GPAP, as described herein, include those sequences with deletions, insertions, or substitutions of different nucleotides, resulting in a polynucleotide the same as GPAP or a polypeptide with at least one functional characteristic of GPAP. Included within this definition are polymorphisms which may or may not be readily detectable using a particular oligonucleotide probe of the polynucleotide encoding GPAP, and improper or unexpected hybridization to allelic variants, with a locus other than the normal chromosomal locus for the polynucleotide sequence encoding GPAP. The encoded protein may also be "altered," and may contain deletions, insertions, or substitutions of amino acid residues which produce a silent change and result in a functionally equivalent GPAP. Deliberate amino acid substitutions may be made on the basis of similarity in polarity, charge, solubility, hydrophobicity, hydrophilicity, and/or the amphipathic nature of the residues, as long as the biological or immunological activity of GPAP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of GPAP which are preferably about 5 to about 15 amino acids in length, most preferably 14 amino acids, and which retain some biological activity or immunological activity of GPAP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) PCR Primer, a Laboratory Manual, Cold Spring Harbor Press, Plainview, N.Y., pp. 1–5.)

The term "antagonist," as it is used herein, refers to a molecule which, when bound to GPAP, decreases the amount or the duration of the effect of the biological or immunological activity of GPAP. Antagonists may include proteins, nucleic acids, carbohydrates, antibodies, or any other molecules which decrease the effect of GPAP.

As used herein, the term "antibody" refers to intact molecules as well as to fragments thereof, such as Fab, F(ab')$_2$, and Fv fragments, which are capable of binding the epitopic determinant. Antibodies that bind GPAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic GPAP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding GPAP or fragments of GPAP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding GPAP, by Northern analysis is indicative of the presence of nucleic acids encoding GPAP in a sample, and thereby correlates with expression of the transcript from the polynucleotide encoding GPAP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of GPAP. For example, modulation may cause an increase or a decrease in protein activity, binding characteristics, or any other biological, functional, or immunological properties of GPAP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding GPAP, or fragments thereof, or GPAP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formrnamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of GPAP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

THE INVENTION

The invention is based on the discovery of new human GTPase-associated proteins (GPAP), the polynucleotides encoding GPAP, and the use of these compositions for the diagnosis, treatment, or prevention of cell proliferation disorders, autoimmune/inflammatory disorders, and vesicle trafficking disorders.

Nucleic acids encoding the GPAP-1 of the present invention were first identified in Incyte Clone 059953 from the lung cDNA library (LUNGNOT01) using a computer search, e.g., BLAST, for amino acid sequence alignments. A consensus sequence, SEQ ID NO:2, was derived from the following overlapping and/or extended nucleic acid sequences: Incyte Clones 059953 (LUNGNOT01), 922561 (RATRNOT02), and 1989615 (CORPNOT02).

In one embodiment, the invention encompasses a polypeptide comprising the amino acid sequence of SEQ ID NO:1, as shown in FIGS. 1A, 1B, 1C, and 1D. GPAP-1 is 375 amino acids in length and has two potential N-glycosylation sites at residues N77 and N202; four potential casein kinase II phosphorylation sites at residues S63, T169, T200, and S329; and nine potential protein kinase C phosphorylation sites at residues T104, T129, T175, T230, T258, T315, S316, S347, and T364. GPAP-1 has seven potential WD-repeat conserved core consensus sequences from about L62 to about V95, from about L105 to about S138, from about L147 to about I181, from about T189 to about L222, from about M231 to about V264, from about V281 to about T314, and from about L323 to about F356. As shown in FIGS. 3A and 1B, GPAP-1 has chemical and structural homology with Arabidopsis thaliana beta transducin isolog (GI 2281093; SEQ ID NO:5). In particular, GPAP-1 and Arabidopsis thaliana beta transducin isolog share 56% identity. A fragment of SEQ ID NO:2 from about nucleotide 55 to about nucleotide 84 is useful for example, as a hybridization probe. Northern analysis shows the expression of this sequence in various libraries, at least 44% of which are immortalized or cancerous, at least 27% of which involve immune response, and at least 29% are from fetal or proliferating cells. Of particular note is the expression of GPAP-1 in tissues derived from reproductive, cardiovascular, urologic, hematopoietic/immune, developmental, and nervous tissues.

Nucleic acids encoding the GPAP-2 of the present invention were first identified in Incyte Clone 2908824 from the thymus cDNA library (THYMNOT05) using a computer search, e.g., BLAST, for arnino acid sequence alignments. A consensus sequence, SEQ ID NO:4, was derived from the following overlapping and/or extended nucleic acid sequences: Incyte Clones 736131 (TONSNOT01), 1578690 (DUODNOT01), and 2908824 (THYMNOT05).

In one embodiment, the invention encompasses a polypeptide comprising the amino acid sequence of SEQ ID NO:3, as shown in FIGS. 2A, 2B, and 2C. GPAP-2 is 129 amino acids in length and has two potential transmembrane sequences from about I45 to about L63 and from about L103 to about F122. As shown in FIG. 4, GPAP-2 has chemical and structural similarity with human putative Rab5-interacting protein {clone L1-57} (GI 1911774; SEQ ID NO:6). In particular, GPAP-2 and human putative Rab5-interacting protein {clone L1-57} share 68% identity. A fragment of SEQ ID NO:4 from about nucleotide 148 to about nucleotide 174 is useful for example, as a hybridization probe. Northern analysis shows the expression of this sequence in various libraries, at least 46% of which are immortalized or cancerous, at least 38% of which involve immune response, and at least 17% of which are from fetal or proliferating cells. Of particular note is the expression of GPAP-2 in libraries derived from gastrointestinal, reproductive, hematopoietic/immune, and cardiovascular tissues.

The invention also encompasses GPAP variants. A preferred GPAP variant is one which has at least about 80%, more preferably at least about 90%, and most preferably at least about 95% amino acid sequence identity to the GPAP amino acid sequence, and which contains at least one functional or structural characteristic of GPAP.

The invention also encompasses polynucleotides which encode GPAP. In a particular embodiment, the invention encompasses a polynucleotide sequence comprising the sequence of SEQ ID NO:2, as shown in FIGS. 1A, 1B, 1C, and 1D, which encodes a GPAP. In a further embodiment, the invention encompasses the polynucleotide sequence comprising the sequence of SEQ ID NO:4, as shown in FIGS. 2A, 2B, and 2C, which encodes a GPAP.

The invention also encompasses a variant of a polynucleotide sequence encoding GPAP. In particular, such a variant polynucleotide sequence will have at least about 80%, more preferably at least about 90%, and most preferably at least about 95% polynucleotide sequence identity to the polynucleotide sequence encoding GPAP. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of GPAP.

It will be appreciated by those skilled in the art that as a result of the degeneracy of the genetic code, a multitude of polynucleotide sequences encoding GPAP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GPAP, and all such variations are to be considered as being specifically disclosed.

Although nucleotide sequences which encode GPAP and its variants are preferably capable of hybridizing to the nucleotide sequence of the naturally occurring GPAP under appropriately selected conditions of stringency, it may be advantageous to produce nucleotide sequences encoding GPAP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GPAP and its derivatives without altering the encoded amino acid sequences include the production of RNA transcripts having more desirable properties, such as a greater half-life, than transcripts produced from the naturally occurring sequence.

The invention also encompasses production of DNA sequences which encode GPAP and GPAP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding GPAP or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4, under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, the process is automated with machines such as the Hamilton Micro Lab 2200 (Hamilton, Reno, Nev.), Peltier Thermal Cycler (PTC200; M J Research, Watertown, Mass.) and the ABI Catalyst and 373 and 377 DNA Sequencers (Perkin Elmer).

The nucleic acid sequences encoding GPAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode GPAP may be cloned in recombinant DNA molecules that direct expression of GPAP, or fragments or functional equivalents thereof, in appropriate host cells. Due to the inherent degeneracy of the genetic code, other DNA sequences which encode substantially the same or a functionally equivalent amino acid sequence may be produced and used to express GPAP.

The nucleotide sequences of the present invention can be engineered using methods generally known in the art in order to alter GPAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding GPAP may be synthesized, in whole or in part, using chemical methods well known in the art. (See, e.g., Caruthers, M. H. et al. (1980) Nucl. Acids Symp. Ser. 7:215–223, and Horn, T. et al. (1980) Nucl. Acids Symp. Ser. 7:225–232.) Alternatively, GPAP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 43 1A Peptide Synthesizer (Perkin Elmer). Additionally, the amino acid sequence of GPAP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins. Structures and Molecular Properties*, W H Freeman and Co., New York, N.Y.)

In order to express a biologically active GPAP, the nucleotide sequences encoding GPAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding GPAP. Such elements may vary in their strength and specificity. Specific initiation signals may also be used to achieve more efficient translation of sequences encoding GPAP. Such signals include the ATG initiation codon and adjacent sequences, e.g. the Kozak sequence. In cases where sequences encoding GPAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding GPAP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding GPAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding GPAP. For example, routine cloning, subcloning, and propagation of polynucleotide sequences encoding GPAP can be achieved using a multifunctional *E. coli* vector such as Bluescript® (Stratagene) or pSport1™ plasmid (Gibco BRL). Ligation of sequences encoding GPAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of GPAP are needed, e.g. for the production of antibodies, vectors which direct high level expression of GPAP may be used. For example, vectors containing the strong, inducible T5 or T7 bacteriophage promoter may be used.

Yeast expression systems may be used for production of GPAP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of GPAP. Transcription of sequences encoding GPAP may be driven viral promoters, e.g., the 35S and 19S promoters of CaMV used alone or in combination with the omega leader sequence from T M V. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding GPAP may be ligated into an adenovirus transcription/translation complex consisting of the late promoter and tripartite leader sequence. Insertion in a non-essential E1 or E3 region of the viral genome may be used to obtain infective virus which expresses GPAP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of GPAP in cell lines is preferred. For example, sequences encoding GPAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, CA), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding GPAP is inserted within a marker gene sequence, transformed cells containing sequences encoding GPAP can be identified by the absence of marker gene function. Alternatively, a marker gene can be placed in tandem with a sequence encoding GPAP under the control of a single promoter. Expression of the marker gene in response to induction or selection usually indicates expression of the tandem gene as well.

In general, host cells that contain the nucleic acid sequence encoding GPAP and that express GPAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of GPAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GPAP is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GPAP include oligolabeling, nick translation, end-labeling, or PCR amplification using a labeled nucleotide. Alternatively, the sequences encoding GPAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GPAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode GPAP may be designed to contain signal sequences which direct secretion of GPAP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding GPAP may be ligated to a heterologous sequence resulting in translation of a fusion protein in any of the aforementioned host systems. For example, a chimeric GPAP protein containing a heterologous moiety that can be recognized by a commercially available antibody may facilitate the screening of peptide libraries for inhibitors of GPAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the GPAP encoding sequence and the heterologous protein sequence, so that GPAP may be cleaved away from the heterologous moiety following purification. Methods for fusion protein expression and purification are discussed in Ausubel, F. M. et al. (1995 and periodic supplements) Current Protocols in Molecular Biology, John Wiley & Sons, New York, N.Y., ch 10. A variety of commercially available kits may also be used to facilitate expression and purification of fusion proteins.

In a further embodiment of the invention, synthesis of radiolabeled GPAP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of GPAP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431 A peptide synthesizer (Perkin Elmer). Various fragments of GPAP may be synthesized separately and then combined to produce the full length molecule.

THERAPEUTICS

Chemical and structural similarity exists between GPAP-1 and beta transducin isolog from *Arabidopsis thaliana* (GI 2281093). In addition, GPAP-1 is expressed in cancerous, inflamed, fetal or proliferating, reproductive, cardiovascular, urologic, hematopoietic/immune, developmental, and nervous tissues. Therefore, GPAP-1 appears to play a role in cell proliferation disorders and autoimmune/inflammatory disorders.

Chemical and structural similarity exists between GPAP-2 and putative Rab5-interacting protein {clone L1-57} from human (GI 1911774). In addition, GPAP-2 is expressed in cancerous, inflamed, fetal or proliferating, gastrointestinal, reproductive, hematopoietic/immune, and cardiovascular tissues. Therefore, GPAP-2 appears to play a role in cell proliferation disorders, autoimmune/inflammatory disorders, and vesicle trafficking disorders.

Therefore, in one embodiment, GPAP or a fragment or derivative thereof may be administered to a subject to treat or prevent a cell proliferation disorder associated with the decreased expression or activity of a GPAP. Such cell proliferation disorders can include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing GPAP or a fragment or derivative thereof may be administered to a subject to treat or prevent a cell proliferation disorder associated with the decreased expression or activity of a GPAP including, but not limited to, those described above.

In a further embodiment, a pharmaceutical composition comprising a substantially purified GPAP in conjunction with a suitable pharmaceutical carrier may be administered to a subject to treat or prevent a cell proliferation disorder associated with the decreased expression or activity of a GPAP including, but not limited to, those provided above.

In still another embodiment, an agonist which modulates the activity of GPAP may be administered to a subject to treat or prevent a cell proliferation disorder associated with the decreased expression or activity of a GPAP including, but not limited to, those listed above.

In a further embodiment, an antagonist of GPAP may be administered to a subject to treat or prevent a cell proliferation disorder associated with the increased expression or activity of a GPAP. Such a cell proliferation disorder may include, but is not limited to, those described above. In one aspect, an antibody which specifically binds GPAP may be used directly as an antagonist or indirectly as a targeting or delivery mechanism for bringing a pharmaceutical agent to cells or tissue which express GPAP.

In an additional embodiment, a vector expressing the complement of the polynucleotide encoding GPAP may be administered to a subject to treat or prevent a cell proliferation disorder associated with the increased expression or activity of a GPAP including, but not limited to, those described above.

Therefore, in one embodiment, GPAP or a fragment or derivative thereof may be administered to a subject to treat or prevent an autoimmune/inflammatory disorder associated with the decreased expression or activity of a GPAP. Such autoimmune/inflammatory disorders can include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing GPAP or a fragment or derivative thereof may be administered to a subject to treat or prevent an autoimmune/inflammatory disorder associated with the decreased expression or activity of a GPAP including, but not limited to, those described above.

In a further embodiment, a pharmaceutical composition comprising a substantially purified GPAP in conjunction with a suitable pharmaceutical carrier may be administered to a subject to treat or prevent an autoimmune/inflammatory disorder associated with the decreased expression or activity of a GPAP including, but not limited to, those described above.

In still another embodiment, an agonist which modulates the activity of GPAP may be administered to a subject to treat or prevent an autoimmune/inflammatory disorder associated with the decreased expression or activity of a GPAP including, but not limited to, those listed above.

In a further embodiment, an antagonist of GPAP may be administered to a subject to treat or prevent an autoimmune/inflammatory disorder associated with the increased expression or activity of a GPAP. Such an autoimmune/inflammatory disorder may include, but is not limited to, those discussed above. In one aspect, an antibody which specifically binds GPAP may be used directly as an antagonist or indirectly as a targeting or delivery mechanism for bringing a pharmaceutical agent to cells or tissue which express GPAP.

In an additional embodiment, a vector expressing the complement of the polynucleotide encoding GPAP may be administered to a subject to treat or prevent an autoimmune/inflammatory disorder associated with the increased expression or activity of a GPAP including, but not limited to, those described above.

Therefore, in one embodiment, GPAP-2 or a fragment or derivative thereof may be administered to a subject to treat or prevent a vesicle trafficking disorder. Such vesicle trafficking disorders can include, but are not limited to, cystic fibrosis, glucose-galactose malabsorption syndrome, hypercholesterolemia, diabetes mellitus, diabetes insipidus, hyper-and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminthic, and protozoal infections.

In another embodiment, a vector capable of expressing GPAP-2 or a fragment or derivative thereof may be administered to a subject to treat or prevent a vesicle trafficking disorder including, but not limited to, those described above.

In a further embodiment, a pharmaceutical composition comprising a substantially purified GPAP-2 in conjunction with a suitable pharmaceutical carrier may be administered to a subject to treat or prevent a vesicle trafficking disorder including, but not limited to, those described above.

In still another embodiment, an agonist which modulates the activity of GPAP-2 may be administered to a subject to treat or prevent a vesicle trafficking disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GPAP may be produced using methods which are generally known in the art. In particular, purified GPAP may be used to produce antibodies or to screen libraries of pharmaceutical agents to identify those which specifically bind GPAP. Antibodies to GPAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats,rabbits, rats, mice, humans, and others may be immunized by injection with GPAP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and Corynebacterium parvum are especially preferable.

It is preferred that the oligopeptides, peptides, or fragments used to induce antibodies to GPAP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of GPAP amino acids may be fused with those of another protein, such as KLH, and antibodies to the chimeric molecule may be produced.

Monoclonal antibodies to GPAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce GPAP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for GPAP may also be generated. For example, such fragments include, but are not limited to, F(ab')2 fragments produced by pepsin digestion of the antibody molecule and Fab fragments generated by reducing the disulfide bridges of the F(ab)2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GPAP and its specific antibody. A two-site, monoclonal-based immunoassay utilizing monoclonal antibodies reactive to two non-interfering GPAP epitopes is preferred, but a competitive binding assay may also be employed. (Maddox, supra.)

In another embodiment of the invention, the polynucleotides encoding GPAP, or any fragment or complement thereof, may be used for therapeutic purposes. In one aspect, the complement of the polynucleotide encoding GPAP may be used in situations in which it would be desirable to block the transcription of the MRNA. In particular, cells may be transformed with sequences complementary to polynucleotides encoding GPAP. Thus, complementary molecules or fragments may be used to modulate GPAP activity, or to achieve regulation of gene function. Such technology is now well known in the art, and sense or antisense oligonucleotides or larger fragments can be designed from various locations along the coding or control regions of sequences encoding GPAP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding GPAP. (See, e.g., Sambrook, supra; and Ausubel, supra.)

Genes encoding GPAP can be turned off by transforming a cell or tissue with expression vectors which express high levels of a polynucleotide, or fragment thereof, encoding GPAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding GPAP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding GPAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GPAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of GPAP, antibodies to GPAP, and mimetics, agonists, antagonists, or inhibitors of GPAP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 MM to 50 MM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of GPAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example GPAP or fragments thereof, antibodies of GPAP, and agonists, antagonists or inhibitors of GPAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GPAP may be used for the diagnosis of disorders characterized by expression of GPAP, or in assays to monitor patients being treated with GPAP or agonists, antagonists, or inhibitors of GPAP. Antibodies useful for diagnostic purposes may be prepared in the same manner as described above for therapeutics. Diagnostic assays for GPAP include methods which utilize the antibody and a label to detect GPAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring GPAP, including ELISAs, RIAs, and FACS, are known in the art and provide a basis for diagnosing altered or abnormal levels of GPAP expression. Normal or standard values for GPAP expression are established by combining body fluids or cell extracts taken from normal mammalian subjects, preferably human, with antibody to GPAP under conditions suitable for complex formation The amount of standard complex formation may be quantitated by various methods, preferably by photometric means. Quantities of GPAP expressed in subject samples, control, and disease, from biopsied tissues are compared with the standard values. Deviation between standard and subject values establishes the parameters for diagnosing disease.

In another embodiment of the invention, the polynucleotides encoding GPAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GPAP may be correlated with disease. The diagnostic assay may be used to determine absence, presence, and excess expression of GPAP, and to monitor regulation of GPAP levels during therapeutic intervention.

In one aspect, hybridization with PCR probes which are capable of detecting polynucleotide sequences, including genomic sequences, encoding GPAP or closely related molecules may be used to identify nucleic acid sequences which encode GPAP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding GPAP, allelic variants, or related sequences.

Probes may also be used for the detection of related sequences, and should preferably have at least 50% sequence identity to any of the GPAP encoding sequences. The hybridization probes of the subject invention may be DNA or RNA and may be derived from the sequence of SEQ ID NO:2 and SEQ ID NO:4 or from genomic sequences including promoters, enhancers, and introns of the GPAP gene.

Means for producing specific hybridization probes for DNAs encoding GPAP include the cloning of polynucleotide sequences encoding GPAP or GPAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding GPAP may be used for the diagnosis of a disorder associated with expression of GPAP. Examples of such a disorder include, but are not limited to, cell proliferation disorders such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and vesicle trafficking disorders such as cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis, gastric and duodenal ulcers; other conditions associated with abnormal vesicle trafficking, including acquired immunodeficiency syndrome (AIDS); allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminthic, and protozoal infections. The polynucleotide sequences encoding GPAP may be used in Southern or Northern analysis, dot blot, or other membrane-based technologies; in PCR technologies; in dipstick, pin, and ELISA assays; and in microarrays utilizing fluids or tissues from patients to detect altered GPAP expression. Such qualitative or quantitative methods are well known in the art.

In a particular aspect, the nucleotide sequences encoding GPAP may be useful in assays that detect the presence of associated disorders, particularly those mentioned above. The nucleotide sequences encoding GPAP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding GPAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of GPAP, a normal or standard profile for expression is established. This may be accomplished by combining body fluids or cell extracts taken from normal subjects, either animal or human, with a sequence, or a fragment thereof, encoding GPAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GPAP may involve the use of PCR. These oligomers may be chemically synthesized, generated enzymatically, or produced in vitro. Oligomers will preferably contain a fragment of a polynucleotide encoding GPAP, or a fragment of a polynucleotide complementary to the polynucleotide encoding GPAP, and will be employed under optimized conditions for identification of a specific gene or condition. Oligomers may also be employed under less stringent conditions for detection or quantitation of closely related DNA or RNA sequences.

Methods which may also be used to quantitate the expression of GPAP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding GPAP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C.M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding GPAP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, GPAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GPAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with GPAP, or fragments thereof, and washed. Bound GPAP is then detected by methods well known in the art. Purified GPAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GPAP specifically compete with a test compound for binding GPAP. In this manner, antibodies can be used to detect the presence of any peptide which shares one or more antigenic determinants with GPAP.

In additional embodiments, the nucleotide sequences which encode GPAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

LUNGNOT01

The LUNGNOT01 human lung cDNA library was purchased from Stratagene (Catalog # STR937210). The lung tissue had been removed from a 72-year-old male during surgery for lung cancer. The custom-constructed library phage particles were infected into *E. coli* host strain XL1-Blue® (Stratagene).

THYMNOT05

The THYMNOT05 cDNA library was constructed from microscopically normal thymus gland tissue obtained from a 3 year-old Spanish male. The patient presented with severe pulmonary stenosis and cyanosis. Patient history included Blalock Taussig Shunt and pulmonary valvotomy. The frozen tissue was homogenized and lysed in TRIzol reagent (1 g tissue/10 ml TRIzol; Cat. #10296–028; GIBCO BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The mRNA was re-extracted twice with acid phenol-chloroform pH 4.7 and precipitated using 0.3M sodium acetate and 2.5 volumes ethanol. The mRNA was then isolated using the Qiagen Oligotex kit (QIAGEN, Inc., Chatsworth, Calif.) and used to construct the cDNA library.

The mRNA was handled according to the recommended protocols in SuperScript™, a plasmid system for cDNA synthesis and plasmid cloning (Cat. #18248–013, GIBCO BRL).The cDNAs were fractionated on a Sepharose CL4B column (Cat. #275105–01; Pharmacia), and those cDNAs exceeding 400 bp were ligated into pINCY 1. The plasmid pINCY 1 was subsequently transformed into DH5α™ competent cells (Cat. #18258–012; GIBCO BRL).

II. Isolation and Sequencing of cDNA Clones

LUNGNOT01

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single-stranded circular phagemid DNA molecule that included all DNA sequences of the pBluescript® plasmid and the cDNA insert. The phagemid DNA was secreted from the cells and purified, then used to re-infect fresh host cells, where the double-stranded phagemid DNA was produced. Because the phagemid carries the gene for β-lactamase, the newly-transformed bacteria are selected on medium containing ampicillin.

Phagemid DNA was purified using the Magic Minipreps™ DNA Purification System (Promega Cat. #A7100). Phagemid DNA was also purified using the QIAwell-8 Plasmid Purification System from QIAGEN®, QLAwell PLUS, and QLAwell ULTRA DNA Purification System (QIAGEN, Inc.). The cDNA inserts from random isolates of the various libraries were sequenced by the method of Sanger and Coulson (Sanger, F. and Coulson, A. R. (1975) J. Mol. Biol. 94:441f) using machines such as the Catalyst 800 or a Hamilton Micro Lab 2200 (Hamilton, Reno Nev.) in combination with four Peltier Thermal Cyclers (PTC200 from M J Research, Watertown Mass.) and the Applied Biosystems 377 or 373 DNA sequencers, and the reading frame was determined.

THYMNOT05

Plasmid DNA was released from the cells and purified using the REAL Prep 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from M J Research, Watertown, Mass.) and Applied Biosystems 377 DNA Sequencing Systems, and the reading frame was determined.

III. Similarity Searching of cDNA Clones and Their Deduced Proteins

LUNGNOT01

The first algorithm was originally developed by D. J. Lipman and W. R. Pearson, (1985, Science 227:1435). In this algorithm, the homologous regions of the nucleotide sequences are searched in a two step manner. In the first step, the highest homologous regions are determined by calculating a matching score using a homology score table. The parameter 'Ktup' is used in this step to establish the minimum window size to be shifted for comparing two sequences. Ktup also sets the number of bases that must match to extract the highest homologous region among the sequences. In this step, no insertions or deletions are applied and the homology is displayed as an initial (INIT) value.

In the second step, the homologous regions are aligned to obtain the highest matching score by inserting a gap in order to add a probable deleted portion. The matching score obtained in the first step is recalculated using the homology score Table and the insertion score Table to an optimized (OPT) value in the final output.

DNA homologies between two sequences can be examined graphically using the Harr method of constructing dot matrix homology plots. (Needleman, S. B. and Wunsch, C. O. (1970) J. Mol. Biol 48:443.) This method produces a two-dimensional plot which can be useful in determining regions of homology versus regions of repetition.

The second algorithm was developed by Applied Biosystems Inc. and has been incorporated into the Inherit 670 Sequence Analysis System. In this algorithm, Pattern Specification Language (developed by TRW Inc.) is used to determine regions of homology. There are three parameters that determine how the sequence comparisons are run: window size, window offset, and error tolerance. Using a combination of these three parameters, the DNA database is searched for sequences containing regions of homology and the appropriate sequences are scored with an initial value. Subsequently, these homologous regions are examined using dot matrix homology plots to determine regions of homology versus regions of repetition. Smith-Waterman alignments were used to display the results of the homology search.

Following the search for homologous regions, the sequences from the cDNA clones were classified as to whether they are exact matches (regions of exact homology) homologous human matches (regions of high similarity, but not exact matches), homologous non-human matches (regions of high similarity present in species other than human), or nonmatches (no significant regions of homology to previously identified nucleotide sequences).

Searches of the deduced polypeptides and peptides are done in a manner analogous to that done with the cDNA sequences. The sequence of the polypeptide is used as a query sequence and compared to the previously identified sequences contained in a database such as Swiss/Prot or the NBRF Protein database to find homologous polypeptides. These polypeptides are initially scored for homology using a homology score Table (Orcutt, B. C. and Dayhoff, M. O. Scoring Matrices, PIR Report MAT—0285 (February 1985)) resulting in an INIT score. The homologous regions are aligned to obtain the highest matching scores by inserting a gap which adds a probable deleted portion. The matching score is recalculated using the homology score Table and the insertion score Table resulting in an optimized (OPT) score. Even in the absence of knowledge of the proper reading frame of an isolated sequence, the above-described polypeptide homology search may be performed by searching all 3 reading frames.

Peptide and protein sequence homologies can also be ascertained using the Inherit 670 Sequence Analysis System in an analogous way to that used in DNA sequence homologies. Pattern Specification Language and parameter windows are used to search polypeptide databases for sequences containing regions of homology which are scored with an initial value. Subsequent examination with a dot-matrix homology plot determines regions of homology versus regions of repetition.

THYMNOT05

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 15:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

LUNGNOT01 and THYMNOT05

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. and Henikoff G. J., Nucleic Acids Res. (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0\times10^{-3}$ indicates that the match would occur by chance no more than one time in every 1000 searches. Only those matches with a cutoff score of 1000 or greater and a cutoff probability value of $1.0\times10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Curr. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT . A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \text{maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding GPAP occurs. Abundance and percent abundance are also reported. Abundance directly reflects the number of times a particular transcript is represented in a cDNA library, and percent abundance is abundance divided by the total number of sequences examined in the cDNA library.

V. Extension of GPAP Encoding Polynucleotides

The nucleic acid sequences of Incyte Clones 059953 and 2908824 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2x carb). The following day, several colonies were randomly picked from each plate and cultured in 150 µl of liquid LB/2x carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the GPAP-encoding sequences, or any parts thereof, are used to detect, decrease, or inhibit expression of naturally occurring GPAP. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of GPAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GPAP-encoding transcript.

IX. Expression of GPAP

Expression and purification of GPAP is achieved using bacterial or virus-based expression systems. For expression of GPAP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express GPAP upon induction with isopropyl beta-D-thiogalactopyranoside (IPTG). Expression of GPAP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding GPAP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, GPAP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from GPAP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified GPAP obtained by these methods can be used directly in the following activity assay.

X. Demonstration of GPAP Activity

GPAP-1

GPAP-1 activity may be demonstrated as the ability to stimulate phospholipase C$\beta$2 (PLC$\beta$2) activity in cultured cells transiently transfected with plasmids encoding GPAP-1, G$\gamma$, and PLC$\beta$2. (Katz, A. et al. (1992) Nature 360:686–689; and Berridge, M. J. et al. (1983) Biochem. J. 212:473–482) Plasmids separately encoding GPAP-1, various G$\gamma$ subunits, and PLC$\beta$2 under the control of the cytomegalovirus promoter are co-transfected into cultured COS-7 cells growing in 12-well culture dishes. An equal amount of DNA is added to each well. As a control, COS-7 cells are co-transfected with plasmids encoding GPAP- 1, various G$\gamma$ subunits, and bacterial $\beta$-galactosidase. Twenty-four hours following transfection, the cells are incubated in medium containing 10 $\mu$Ci/ml [2-$^3$H]-myo-inositol (Amersham). Cells are washed 24 hours later with phosphate buffered saline and incubated in 200 $\mu$l inositol-free medium containing 10 mM LiCl. After incubation for 25 minutes at 37° C., 200 $\mu$l cold 10% perchloric acid and 20 $\mu$l phytic acid (20 ml/ml) are added, and the cells are incubated on ice for 10 minutes. Then 200 $\mu$l of solution from a well are transferred to a microcentrifuge tube and neutralized with 2 M KOH. After centrifugation, the supernatant is loaded on a 0.5 ml AG1-X8 anion exchange column (200–400 mesh, formate form; Bio-Rad). The column is washed with distilled water to remove unreacted [2-$^3$H]-myo-inositol. The radiolabeled inositol phosphates are eluted by the stepwise addition of solutions containing increasing levels of formate: 5 mM disodium tetraborate/60 mM sodium formate; 0.1 M formic acid/0.2 M ammonium formate; 0.1 M formic acid/0.4 M ammonium formate; 0.1 M formic acid/1.0 M ammonium formate. 0.5 ml of the combined elution is mixed with 10 ml scintillation cocktail and counted. The radioactive counts are proportional to the PLC$\beta$2 activity in the cells. The difference in PLC$\beta$2 activity between cells transfected with and without PLC$\beta$2 is due to the stimulation by GPAP-1.

GPAP-2

GPAP-2 activity is demonstrated as the ability to interact with the GTPase-deficient mutant Rab5 protein Rab5Q79L. (Vitale (1995) supra.) GPAP-2 is labeled with $^{125}$I Bolton-Hunter reagent. (See, e.g., Bolton et al. (1973) Biochem. J. 133:529.) Aliquots of purified Rab5Q79L, previously arrayed in the wells of a multi-well plate, are incubated with the labeled GPAP-2, washed, and any wells with labeled GPAP-2 complex are assayed. Data obtained using different concentrations of GPAP-2 are used to calculate values for the number, affinity, and association of GPAP-2 with Rab5Q79L.

XI. Functional Assays

GPAP function is assessed by expressing the sequences encoding GPAP at physiologically elevated levels in mammalian cell culture systems. cDNA is subcloned into a mammalian expression vector containing a strong promoter that drives high levels of cDNA expression. Vectors of choice include pCMV SPORT™ (GIBCO BRL, Gaithersburg, Md.) and pCR™ 3.1 (Invitrogen, Carlsbad, Calif., both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface.

Methods in flow cytometry are discussed in Ormerod, M. G. (1994) Flow Cytometry, Oxford, New York, N.Y.

The influence of GPAP on gene expression can be assessed using highly purified populations of cells transfected with sequences encoding GPAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding GPAP and other genes of interest can be analyzed by Northern analysis or microarray techniques.

XII. Production of GPAP Specific Antibodies

GPAP substantially purified using polyacrylamide gel electrophoresis (PAGE)(see, e.g., Harrington, M.G. (1990) Methods Enzymol. 182:488–495), or other purification techniques, is used to immunize rabbits and to produce antibodies using standard protocols.

Alternatively, the GPAP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431 A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring GPAP Using Specific Antibodies

Naturally occurring or recombinant GPAP is substantially purified by immunoaffinity chromatography using antibodies specific for GPAP. An immunoaffinity column is constructed by covalently coupling anti-GPAP antibody to an activated chromatographic resin, such as CNBr-activated Sepharose (Pharmacia & Upjohn). After the coupling, the resin is blocked and washed according to the manufacturer's instructions.

Media containing GPAP are passed over the immunoaffinity column, and the column is washed under conditions that allow the preferential absorbance of GPAP (e.g., high ionic strength buffers in the presence of detergent). The column is eluted under conditions that disrupt antibody/GPAP binding (e.g., a buffer of pH 2 to pH 3, or a high concentration of a chaotrope, such as urea or thiocyanate ion), and GPAP is collected.

XIV. Identification of Molecules Which Interact with GPAP

GPAP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled GPAP, washed, and any wells with labeled GPAP complex are assayed. Data obtained using different concentrations of GPAP are used to calculate values for the number, affinity, and association of GPAP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified non-genomic polynucleotide encoding a polypeptide selected from the group consisting of:
   a) SEQ ID NO:1,
   b) a variant of SEO ID NO:1 having at least 90% identity to SEO ID NO:1 and which, in conjunction with Gγ, stimulates phospholipase Cβ2 activity, and
   c) a fragment of SEQ ID NO:1 from about amino acid residue M1 to about amino acid residue E11 of SEQ ID NO:1.

2. An isolated and purified non-genomic polynucleotide which hybridizes under stringent conditions at 42° C. in 250 mM NaCl and 25 mM trisodium citrate, and wash conditions at 42° C. in 15 mM NaCl and 1.5 mM trisodium citrate to a polynucleotide encoding SEQ ID NO:1, and which encodes a polypeptide which, conjunction with Gγ, stimulates phospholipase Cβ2 activity.

3. An isolated and purified non-genomic polynucleotide having a sequence which is completely complementary to the polynucleotide sequence of claim 1.

4. An isolated and purified polynucleotide comprising a polynucleotide sequence selected from the group consisting of:
   a) SEQ ID NO:2,
   b) a variant of SEQ ID NO:2 having at least 90% identity to SEQ ID NO:2 and which encodes a variant of SEQ ID NO:1 which, in conjunction with Gγ, stimulates phospholipase Cβ2 activiy, and
   c) a fragment of SEQ ID NO:2 from about nucleotide 55 to about nucleotide 84 of SEQ ID NO:2.

5. An isolated and purified non-genomic polynucleotide having a sequence which is completely complementary to the polynucleotide of claim 4.

6. An expression vector comprising the polynucleotide of claim 1.

7. A host cell comprising the expression vector of claim 6.

8. A method for producing a polypeptide, the method comprising the steps of:
   a) culturing the host cell of claim 7 under conditions suitable for the expression of the polypeptide; and
   b) recovering the polypeptide from the host cell culture.

9. A method for detecting a polynucleotide in a sample, the method comprising the steps of:
   (a) hybridizing the polynucleotide of claim 3 to at least one of the nucleic acids in the sample, thereby forming a hybridization complex; and
   (b) detecting the hybridization complex, wherein the presence of the hybridization complex correlates with the presence of the polynucleotide in the sample.

10. The method of claim 9 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 375 amino acids
      (B) TYPE: amino acid
      (C) STRANDEDNESS: single
      (D) TOPOLOGY: linear (vii) IMMEDIATE SOURCE:
      (A) LIBRARY: LUNGNOT01
      (B) CLONE: 059953

(xi) SEQUENCE DESCRIPTION: SEQ ID NO:1:

Met Ile Glu Gln Gln Lys Arg Lys Gly Pro Glu Leu Pro Leu Val Pro
1             5                  10              15

-continued

```
Val Lys Arg Gln Arg His Glu Leu Leu Leu Gly Ala Gly Ser Gly Pro
             20                  25                  30
Gly Ala Gly Gln Gln Gln Ala Thr Pro Gly Ala Leu Leu Gln Ala Gly
         35                  40                  45
Pro Pro Arg Cys Ser Ser Leu Gln Ala Pro Ile Met Leu Leu Ser Gly
     50                  55                  60
His Glu Gly Glu Val Tyr Cys Cys Lys Phe His Pro Asn Gly Ser Thr
 65                  70                  75                  80
Leu Ala Ser Ala Gly Phe Asp Arg Leu Ile Leu Leu Trp Asn Val Tyr
                 85                  90                  95
Gly Asp Cys Asp Asn Tyr Ala Thr Leu Lys Gly His Ser Gly Ala Val
             100                 105                 110
Met Glu Leu His Tyr Asn Thr Asp Gly Ser Met Leu Phe Ser Ala Ser
         115                 120                 125
Thr Asp Lys Thr Val Ala Val Trp Asp Ser Glu Thr Gly Glu Arg Val
    130                 135                 140
Lys Arg Leu Lys Gly His Thr Ser Phe Val Asn Ser Cys Tyr Pro Ala
145                 150                 155                 160
Arg Arg Gly Pro Gln Leu Val Cys Thr Gly Ser Asp Asp Gly Thr Gly
                165                 170                 175
Lys Leu Trp Asp Ile Arg Lys Lys Ala Ala Ile Gln Thr Phe Gln Asn
            180                 185                 190
Thr Tyr Gln Val Leu Ala Val Thr Phe Asn Asp Thr Ser Asp Gln Ile
        195                 200                 205
Ile Ser Gly Gly Ile Asp Asn Asp Ile Lys Val Trp Asp Leu Arg Gln
    210                 215                 220
Asn Lys Leu Thr Tyr Thr Met Arg Gly His Ala Asp Ser Val Thr Gly
225                 230                 235                 240
Leu Ser Leu Ser Ser Glu Gly Ser Tyr Leu Leu Ser Asn Ala Met Asp
                245                 250                 255
Asn Thr Val Arg Val Trp Asp Val Arg Pro Phe Ala Pro Lys Glu Arg
            260                 265                 270
Cys Val Lys Ile Phe Gln Gly Asn Val His Asn Phe Glu Lys Asn Leu
        275                 280                 285
Leu Arg Cys Ser Trp Ser Pro Asp Gly Ser Lys Ile Ala Ala Gly Ser
    290                 295                 300
Ala Asp Arg Phe Val Tyr Val Trp Asp Thr Thr Ser Arg Arg Ile Leu
305                 310                 315                 320
Tyr Lys Leu Pro Gly His Ala Gly Ser Ile Asn Glu Val Ala Phe His
                325                 330                 335
Pro Asp Glu Pro Ile Ile Ile Ser Ala Ser Ser Asp Lys Arg Leu Tyr
            340                 345                 350
Met Gly Glu Phe Ser Glu Asp Met Asp Trp Lys Thr Pro Arg Leu Leu
        355                 360                 365
Val Phe Glu Pro Gln Thr Ala
    370                 375
```

(2) INFORMATION FOR SEQ ID NO:2:

(i) SEQUENCE CHARACTERISTICS:
        (A) LENGTH: 1211 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT01
        (B) CLONE: 059953

(xi) SEQUENCE DESCRIPTION: SEQ ID NO:2:

```
CCCACGCGTC CGCCCACGCG TCCGGCGGCG CTGAAGAGAC CGGTTGCCGC CATGATAGAA      60

CAGCAGAAGC GTAAGGGCCC AGAGTTGCCG CTGGTTCCAG TCAAGCGGCA GCGGCATGAG     120

TTGCTGTTGG GAGCGGGGTC TGGCCCAGGA GCCGGGCAGC AGCAGGCGAC GCCGGGAGCC     180

TTGCTGCAAG CGGGACCTCC AAGATGTTCC TCCCTTCAAG CCCCAATCAT GCTGCTCTCT     240

GGACATGAAG GGGAAGTCTA CTGCTGCAAG TTCCACCCCA ACGGATCCAC CTTAGCATCT     300

GCAGGATTTG ACCGACTGAT ATTACTGTGG AATGTCTATG GTGACTGTGA TAACTATGCC     360

ACACTGAAGG GACACAGTGG AGCAGTGATG GAATTGCATT ACAACACAGA TGGCAGTATG     420

CTTTTCTCAG CATCCACAGA TAAAACCGTG GCTGTGTGGG ATAGTGAAAC AGGTGAGAGG     480

GTTAAAAGGC TAAAGGGACA TACTTCCTTT GTGAATTCCT GTTATCCAGC CAGGAGAGGC     540

CCTCAGCTTG TCTGCACTGG CAGTGACGAT GGCACAGGTA AGCTTTGGGA CATCCGGAAG     600

AAAGCAGCCA TCCAGACATT TCAGAACACG TACCAGGTGT TAGCTGTGAC CTTCAATGAC     660

ACAAGTGATC AGATTATTTC TGGTGGAATA GACAATGATA TCAAGGTCTG GGACCTGCGC     720

CAGAACAAGC TAACCTACAC CATGAGAGGC CATGCAGATT CAGTGACTGG CCTGAGTTTA     780

AGTTCTGAAG GCTCTTATCT TTTGTCCAAT GCAATGGACA ATACAGTTCG TGTCTGGGAT     840

GTCCGGCCAT TTGCCCCCAA AGAGAGATGT GTAAAGATAT TCAAGGAAA TGTGCACAAC     900

TTTGAAAAGA ACCTTCTGAG ATGTTCTTGG TCACCTGATG GAAGCAAAAT AGCAGCTGGC     960

TCAGCCGACA GGTTTGTTTA TGTGTGGGAT ACCACAAGCA GGAGAATATT GTATAAGCTG    1020

CCCGGCCATG CTGGCTCCAT CAATGAAGTG GCTTTCCACC CTGATGAGCC CATCATTATC    1080

TCAGCATCGA GTGACAAGAG ACTGTATATG GGAGAGTTCA GTGAAGATAT GGACTGGAAG    1140

ACTCCAAGGC TGCTTGTCTT TGAGCCTCAG ACTGCATAAG TGATGCCAAT GTTGGATGTC    1200

AGGCTAGCAC C                                                        1211
```

(2) INFORMATION FOR SEQ ID NO:3:

(i) SEQUENCE CHARACTERISTICS:
        (A) LENGTH: 129 amino acids
        (B) TYPE: amino acid
        (C) STRANDEDNESS: single
        (D) TOPOLOGY: linear (vii) IMMEDIATE SOURCE:
        (A) LIBRARY: THYMNOT05
        (B) CLONE: 2908824

(xi) SEQUENCE DESCRIPTION: SEQ ID NO:3:

```
Met Ser Gly Gly Arg Arg Lys Glu Glu Pro Pro Gln Pro Gln Leu Ala
 1               5                  10                  15

Asn Gly Ala Leu Lys Val Ser Val Trp Ser Lys Val Leu Arg Ser Asp
            20                  25                  30

Ala Ala Trp Glu Asp Lys Asp Glu Phe Leu Asp Val Ile Tyr Trp Phe
        35                  40                  45

Arg Gln Ile Ile Ala Val Val Leu Gly Val Ile Trp Gly Val Leu Pro
    50                  55                  60

Leu Arg Gly Phe Leu Gly Ile Ala Gly Phe Cys Leu Ile Asn Ala Gly
65                  70                  75                  80

Val Leu Tyr Leu Tyr Phe Ser Asn Tyr Leu Gln Ile Asp Glu Glu Glu
```

−continued

```
                85                  90                  95
Tyr Gly Gly Thr Trp Glu Leu Thr Lys Glu Gly Phe Met Thr Ser Phe
               100                 105                 110
Ala Leu Phe Met Val Ile Trp Ile Ile Phe Tyr Thr Ala Ile His Tyr
               115                 120                 125
Asp
```

(2) INFORMATION FOR SEQ ID NO:4:

(i) SEQUENCE CHARACTERISTICS:
        (A) LENGTH: 1051 base pairs
        (B) TYPE: nucleic acid
        (C) STRANDEDNESS: single
        (D) TOPOLOGY: linear (vii) IMMEDIATE SOURCE:
        (A) LIBRARY: THYMNOT05
        (B) CLONE: 2908824

(xi) SEQUENCE DESCRIPTION: SEQ ID NO:4:

```
GGCCAGGTTG TGAGGAACCG CAGCGCGCCG CAGGACCGGG CCGCTGAGCC TGCAGCCGCC      60
CCGCGCCGTG ACCTGCGACC CTAGACCCCG ACTCCCTTTG GCTCAGCCCG CGCGCCCCAG     120
GCCCGGCCCG GCGGCGCGA CGGGAGGATG AGCGGCGGGC GGCGGAAGGA GGAGCCGCCT      180
CAGCCGCAGC TGGCCAACGG GGCCCTCAAA GTCTCCGTCT GGAGTAAGGT GCTGCGGAGC     240
GACGCGGCCT GGGAGGATAA GGATGAATTT TTAGATGTGA TCTACTGGTT CCGACAGATC     300
ATTGCTGTGG TCCTGGGTGT CATTTGGGGA GTTTTGCCAT TACGAGGGTT CTTGGGAATA     360
GCAGGATTCT GCCTGATCAA TGCAGGAGTC CTGTACCTCT ACTTCAGCAA TTACCTACAG     420
ATTGATGAGG AAGAATATGG TGGCACGTGG GAGCTCACGA AGGAAGGGTT TATGACCTCT     480
TTTGCCTTGT TCATGGTCAT TTGGATCATC TTTTACACTG CCATCCATTA TGACTGATGG     540
TGTACAGCTC CCAAGTGCTC CCTATCCAGT CCAAAGGACC CTCTTGATTA CAGCACAGGA     600
ACTTGATCGT TGGGGAACCC CAGCCCCTTG GAACTTGGAA GACCCGTGTT TCCTGGACCG     660
CGAATCAGTG TGTTGGGCAT CAGTGTTTTC TGCAAGGGTT GTGACCTGAA ACTTTTTAAA     720
AACCACCCAC CTTTGGGGAA GCATTTCTGA ATTTATCCAT CACCAACCAT TTCTTCTTGG     780
ATACCATCAA GTAACAGCTA TTATTTGCCA AGTGGAGCTG TCATTTAATT TGATGCACCT     840
CTGGATTCAG ATGAAACATT AAATTGTCTT CCTCGATTCT CCATCGGGTG TAGAGTTTTT     900
AAACTATCAA TGGCATTTCA AGTCTTCTGA ACAGCATGG CTGTATGTGC GTGGTCCATA      960
GCACAGTACA TGCAGCATCT AATAAGAGTT TCCATTGTAG AATGTTTTCA CATACTTGAA    1020
TAAATCAAAT CTTTAATTGA GAAAAAAAAA A                                   1051
```

(2) INFORMATION FOR SEQ ID NO:5:

(i) SEQUENCE CHARACTERISTICS:
        (A) LENGTH: 343 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2281093

(xi) SEQUENCE DESCRIPTION: SEQ ID NO:5:

```
Met Glu Ile Met Ser Arg Glu Asn Glu Thr Ala Leu Ser Gly Pro Arg
 1               5                  10                  15
```

```
Pro Met Glu Trp Ser Thr Val Pro His Ser Ala Ser Gln Gly Pro Gly
            20                  25                  30

Pro Asn Gly Lys Asn Arg Thr Ser Leu Glu Ala Pro Ile Met Leu
        35                  40                  45

Leu Ser Gly His Pro Ser Ala Val Tyr Thr Met Lys Phe Asn Pro Ala
        50                  55                  60

Gly Thr Leu Ile Ala Ser Gly Ser His Asp Arg Glu Ile Phe Leu Trp
65                  70                  75                  80

Arg Val His Gly Asp Cys Lys Asn Phe Met Val Leu Lys Gly His Lys
                85                  90                  95

Asn Ala Ile Leu Asp Leu His Trp Thr Ser Asp Gly Ser Gln Ile Val
                100                 105                 110

Ser Ala Ser Pro Asp Lys Thr Val Arg Ala Trp Asp Val Glu Thr Gly
            115                 120                 125

Lys Gln Ile Lys Lys Met Ala Glu His Ser Ser Phe Val Asn Ser Cys
130                 135                 140

Cys Pro Thr Arg Arg Gly Pro Pro Leu Ile Ile Ser Gly Ser Asp Asp
145                 150                 155                 160

Gly Thr Ala Lys Leu Trp Asp Met Arg Gln Arg Gly Ala Ile Gln Thr
                165                 170                 175

Phe Pro Asp Lys Tyr Gln Ile Thr Ala Val Ser Phe Ser Asp Ala Ala
            180                 185                 190

Asp Lys Ile Phe Thr Gly Gly Val Asp Asn Asp Val Lys Val Trp Asp
            195                 200                 205

Leu Arg Lys Gly Glu Ala Thr Met Thr Leu Glu Gly His Gln Asp Thr
210                 215                 220

Ile Thr Gly Met Ser Leu Ser Pro Asp Gly Ser Tyr Leu Leu Thr Asn
225                 230                 235                 240

Gly Met Asp Asn Lys Leu Cys Val Trp Asp Met Arg Pro Tyr Ala Pro
                245                 250                 255

Gln Asn Arg Cys Val Lys Ile Phe Glu Gly His Gln His Asn Phe Glu
            260                 265                 270

Lys Asn Leu Leu Lys Cys Ser Trp Ser Pro Asp Gly Thr Lys Val Thr
            275                 280                 285

Ala Gly Ser Ser Asp Arg Met Val His Ile Trp Asp Thr Thr Ser Arg
290                 295                 300

Arg Thr Ile Tyr Lys Leu Pro Gly His Thr Gly Ser Val Asn Glu Cys
305                 310                 315                 320

Val Phe His Pro Thr Glu Pro Ile Ile Gly Ser Cys Ser Ser Asp Lys
                325                 330                 335

Asn Ile Tyr Leu Gly Glu Ile
                340
```

(2) INFORMATION FOR SEQ ID NO:6:

(i) SEQUENCE CHARACTERISTICS:
        (A) LENGTH: 122 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1911774

(xi) SEQUENCE DESCRIPTION: SEQ ID NO:6:

Pro Trp Ala Asn Gly Ala Ser Lys Ser Pro Ser Gly Val Arg Cys Cys

-continued

```
1               5                   10                  15
Gly Arg Arg Ala Trp Glu Asp Lys Asp Glu Phe Leu Asp Val Ile Tyr
            20                  25                  30
Trp Phe Arg Gln Ile Ile Ala Val Val Leu Gly Val Ile Trp Gly Val
            35              40                  45
Leu Pro Leu Arg Gly Phe Leu Gly Ile Ala Gly Phe Cys Leu Ile Asn
        50              55                  60
Ala Gly Val Leu Tyr Leu Tyr Phe Ser Asn Tyr Leu Gln Ile Asp Glu
65                  70                  75                  80
Glu Glu Tyr Gly Gly Gln Trp Glu Leu Thr Lys Glu Gly Phe Met Pro
                85                  90                  95
Ser Phe Ala Ile Val His Gly His Leu Leu Leu Leu Phe Thr Ser His
                100             105                 110
Pro Tyr Ser Met Met Val Ser Asp Ser Lys
            115                 120
```